United States Patent
Occhipinti

(10) Patent No.: US 9,006,796 B2
(45) Date of Patent: Apr. 14, 2015

(54) METHOD FOR MANUFACTURING A SENSOR DEVICE OF A GASEOUS SUBSTANCE OF INTEREST

(75) Inventor: Luigi Giuseppe Occhipinti, Ragusa (IT)

(73) Assignee: STMicroelectronics S.r.l., Agrate Brianza (IT)

( * ) Notice: Subject to any disclaimer, the term of this patent is extended or adjusted under 35 U.S.C. 154(b) by 526 days.

(21) Appl. No.: 13/278,942

(22) Filed: Oct. 21, 2011

(65) Prior Publication Data

US 2012/0096928 A1    Apr. 26, 2012

(30) Foreign Application Priority Data

Oct. 22, 2010    (IT) .............................. MI2010A1939

(51) Int. Cl.
G01N 27/12         (2006.01)
G01N 27/414        (2006.01)

(52) U.S. Cl.
CPC ................................. G01N 27/4141 (2013.01)

(58) Field of Classification Search
CPC .......... G01N 27/4141; G01N 27/4146; G01N 27/4148
USPC ............................ 73/31.06; 257/253, E21.46
See application file for complete search history.

(56) References Cited

U.S. PATENT DOCUMENTS

| | | | |
|---|---|---|---|
| 4,025,892 A | | 5/1977 | Pompei et al. |
| 6,203,981 B1 | | 3/2001 | Ackley et al. |
| 6,758,962 B1 | * | 7/2004 | Fitzgerald et al. ............ 205/783 |
| 7,053,425 B2 | * | 5/2006 | Sandvik et al. ............... 257/253 |
| 7,112,987 B2 | * | 9/2006 | Frerichs ................... 324/750.02 |
| 7,145,174 B2 | * | 12/2006 | Chiang et al. ................... 257/59 |
| 7,507,618 B2 | * | 3/2009 | Dunbar ......................... 438/197 |
| 7,858,918 B2 | * | 12/2010 | Ludwig ...................... 250/214 A |
| 8,058,647 B2 | * | 11/2011 | Kuwabara et al. .............. 257/43 |
| 8,400,053 B2 | * | 3/2013 | Ward et al. .................... 313/495 |
| 2006/0231882 A1 | * | 10/2006 | Kim et al. ...................... 257/310 |
| 2007/0126021 A1 | * | 6/2007 | Ryu et al. ...................... 257/103 |
| 2008/0221806 A1 | * | 9/2008 | Bryant et al. .................. 702/22 |

(Continued)

FOREIGN PATENT DOCUMENTS

WO    WO 2010115434 A1 * 10/2010 ........... G01N 27/414

OTHER PUBLICATIONS

Farmakis, F.V. et al., "Field-effect transistors with thin ZnO as active layer for gas sensor applications," Microelectronic Engineering 85:1035-1038, 2008.

(Continued)

*Primary Examiner* — Lisa Caputo
*Assistant Examiner* — Punam Roy
(74) *Attorney, Agent, or Firm* — Seed IP Law Group PLLC

(57) ABSTRACT

A method manufactures a sensor device for sensing a gaseous substance and includes a thin film transistor, which includes a source electrode, a drain electrode and a gate electrode; and an element sensitive to the gaseous substance. In particular, the method includes: forming a first metallic layer on a substrate; defining and patterning the first metallic layer for realizing the gate electrode; depositing a dielectric layer above the gate electrode; depositing a second metallic layer above the layer of dielectric material, defining and patterning the second metallic layer for realizing the source electrode and the drain electrode, and forming the sensitive element by filling a channel region of the thin film transistor with an active layer sensitive to the gaseous substance.

27 Claims, 11 Drawing Sheets

(56) References Cited

U.S. PATENT DOCUMENTS

2009/0066345 A1* 3/2009 Klauk et al. .................. 324/661
2010/0050745 A1   3/2010 Liu et al.
2010/0059755 A1   3/2010 Anthopoulos et al.
2011/0113859 A1* 5/2011 Anthopoulos et al. ....... 73/31.06
2012/0058597 A1* 3/2012 Anthopoulos et al. ........ 438/104
2012/0090381 A1* 4/2012 Andersson .................. 73/31.06

OTHER PUBLICATIONS

Gioffré, M. et al., "The influence of oxygen on the optical properties of RF-sputtered zinc oxide thin films," Superlattices and Microstructures 42:85-88, 2007.

* cited by examiner

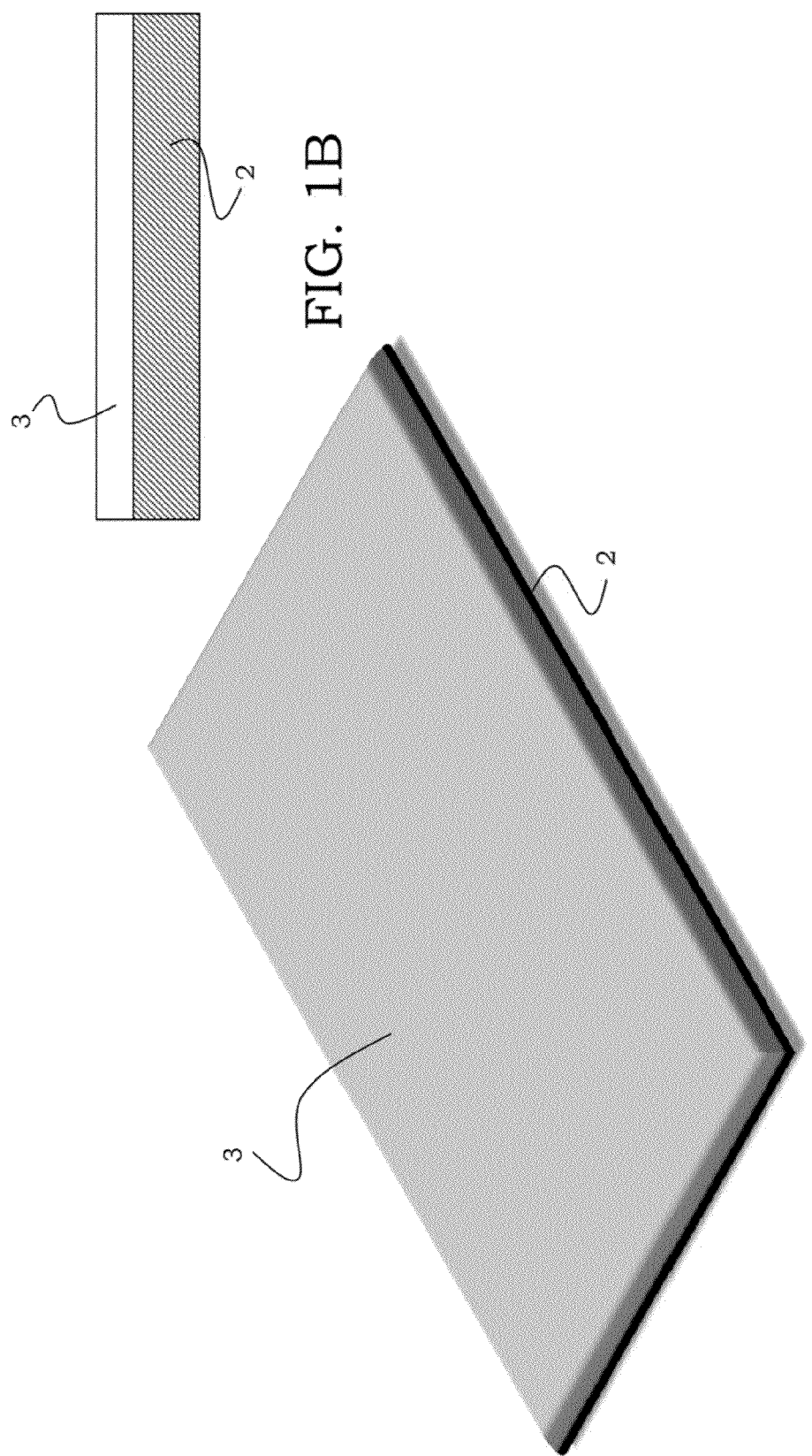

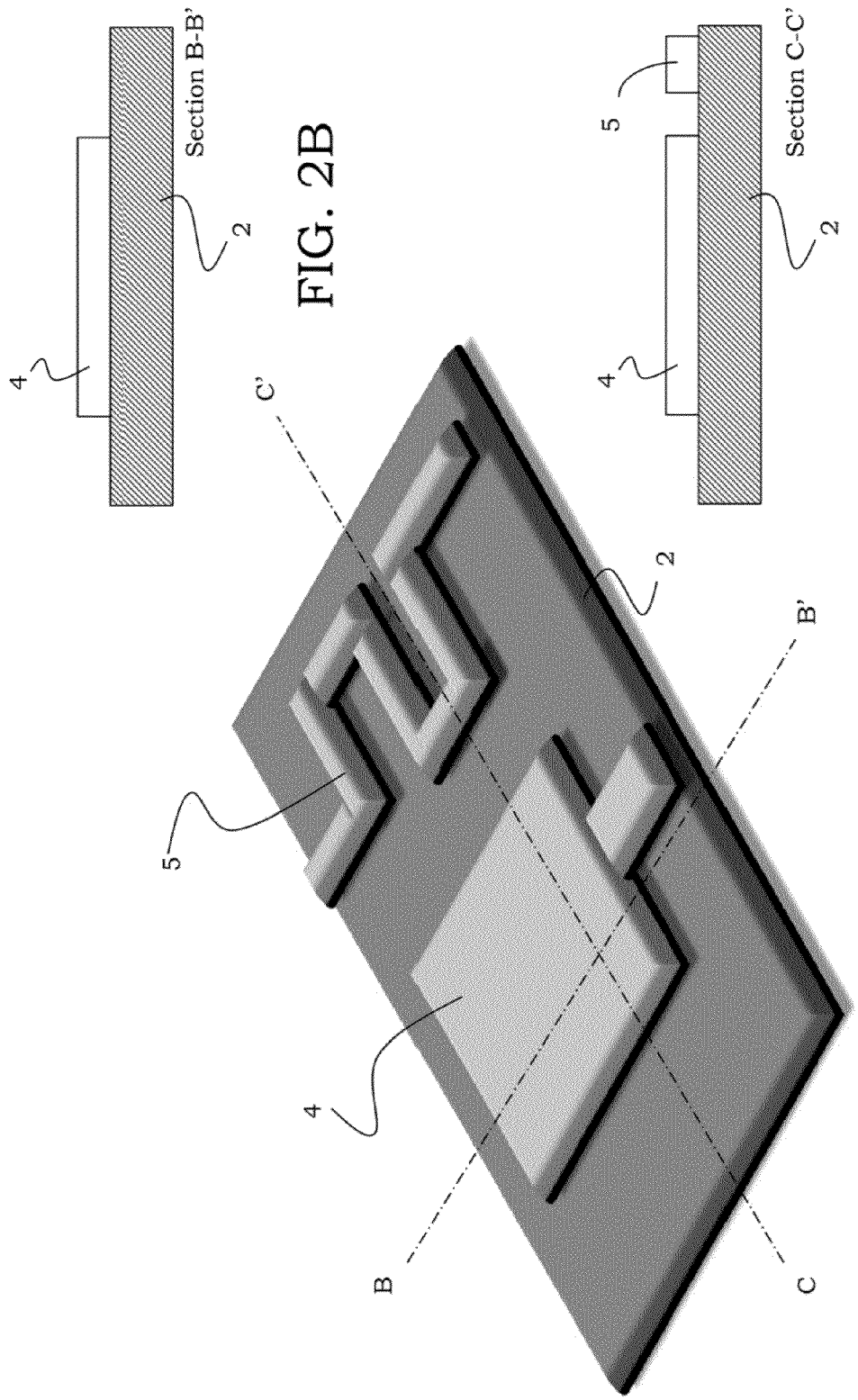

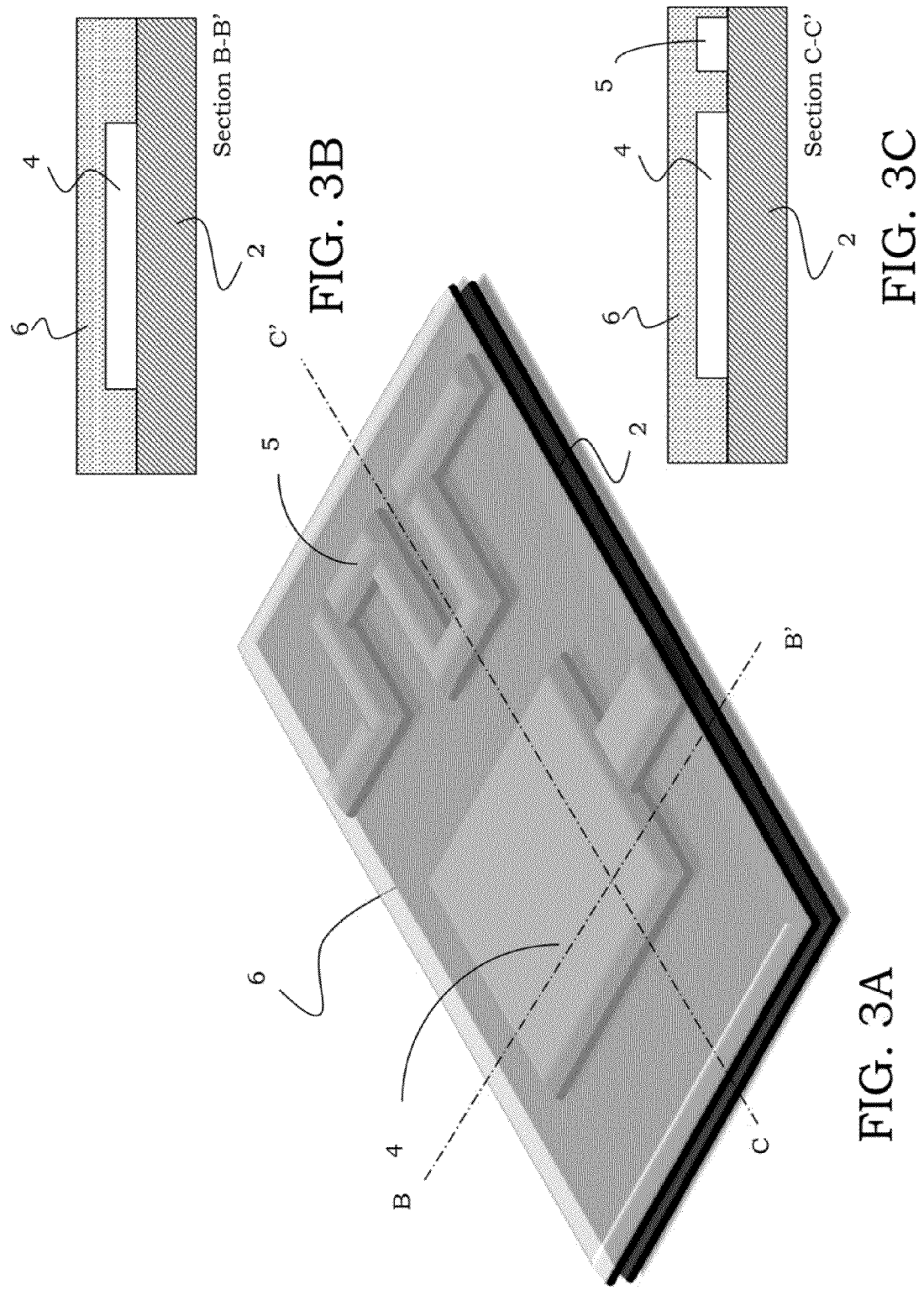

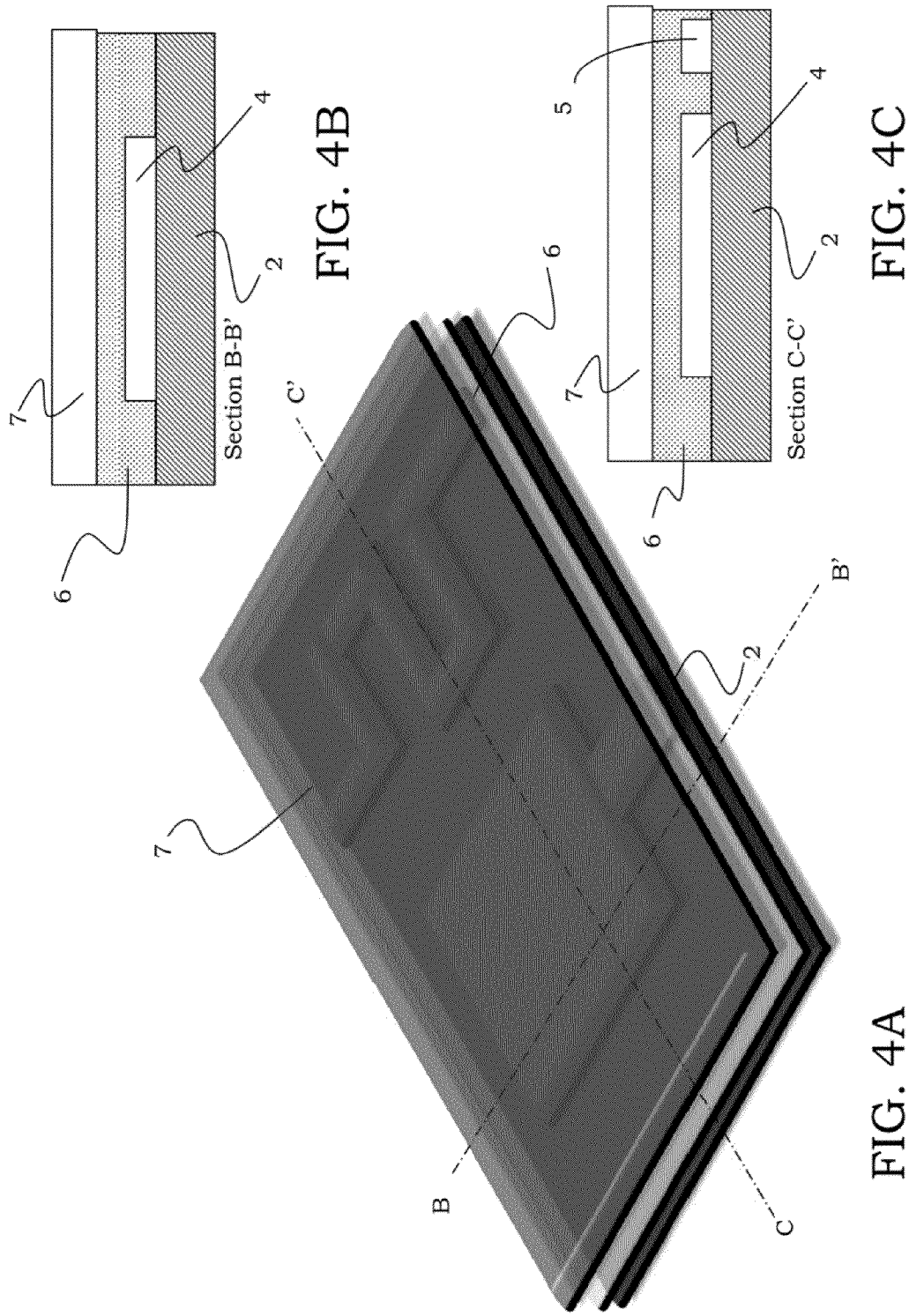

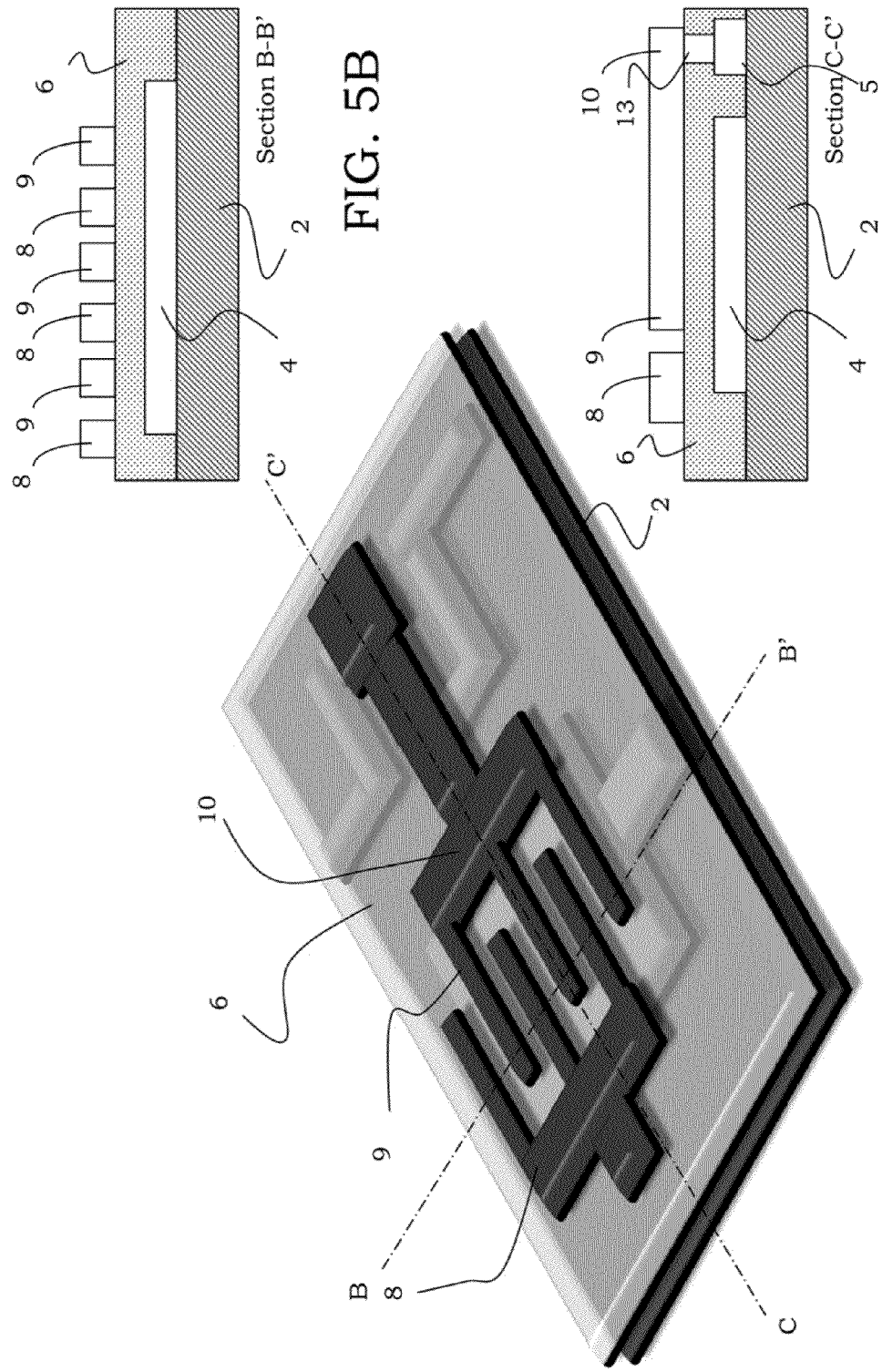

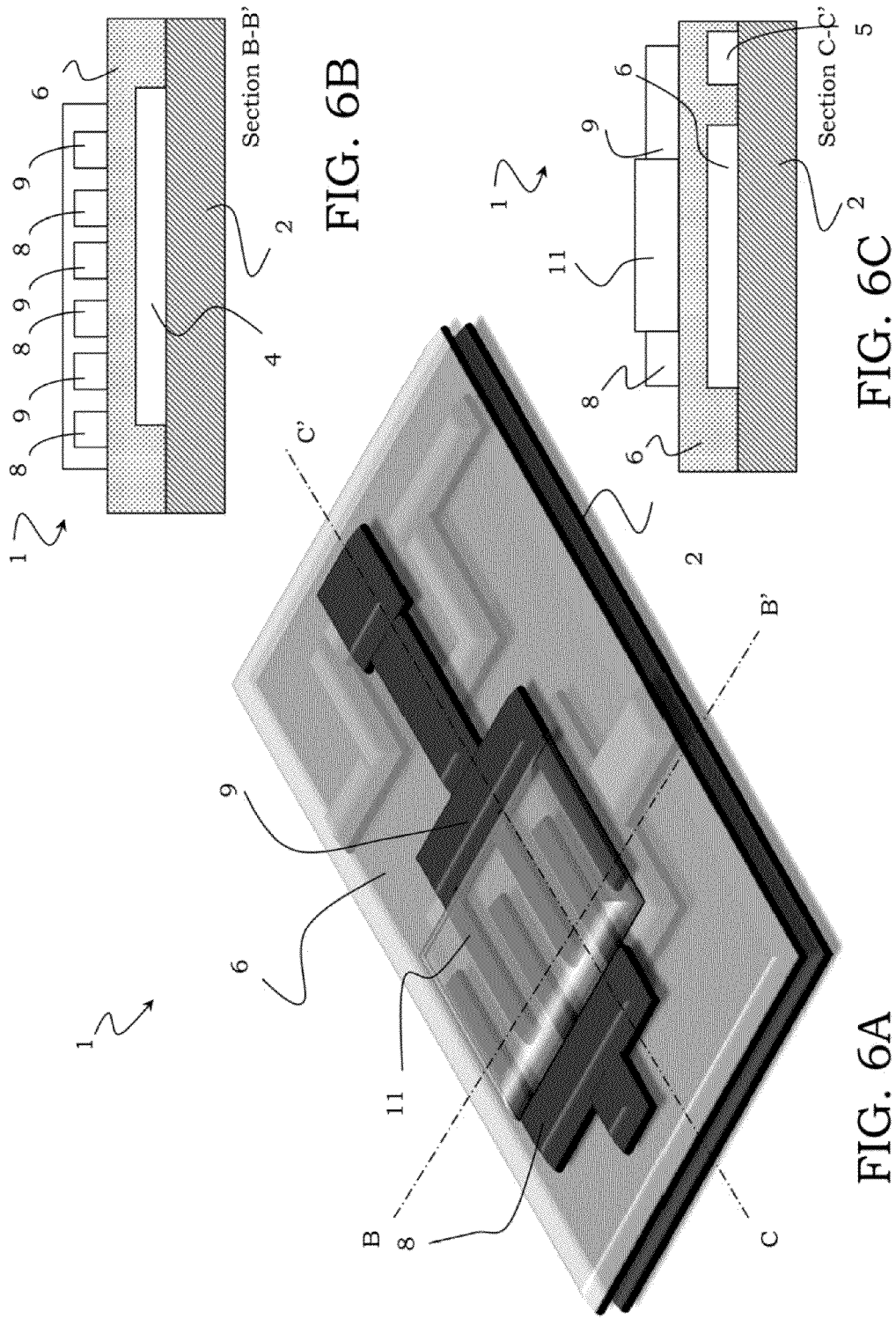

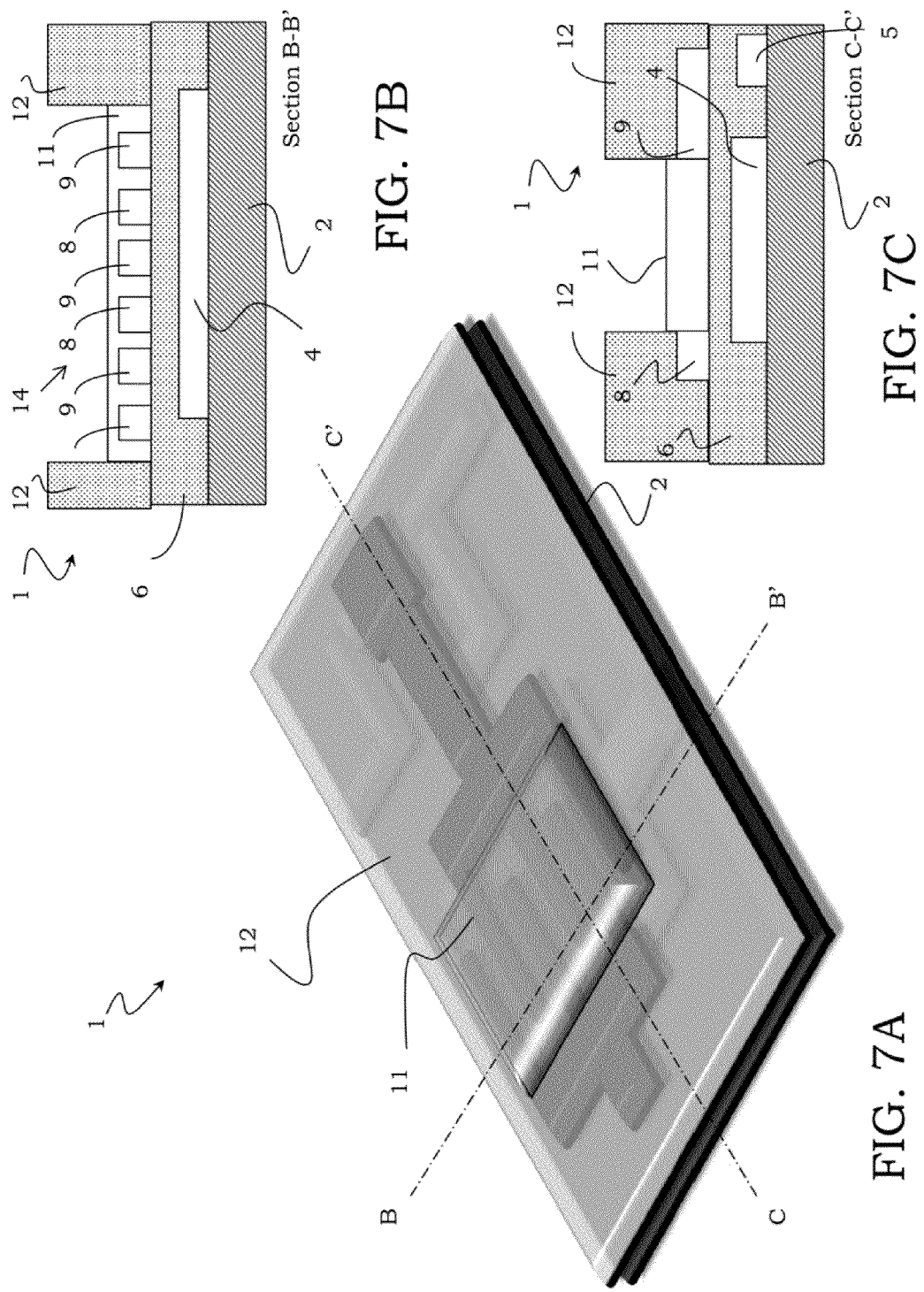

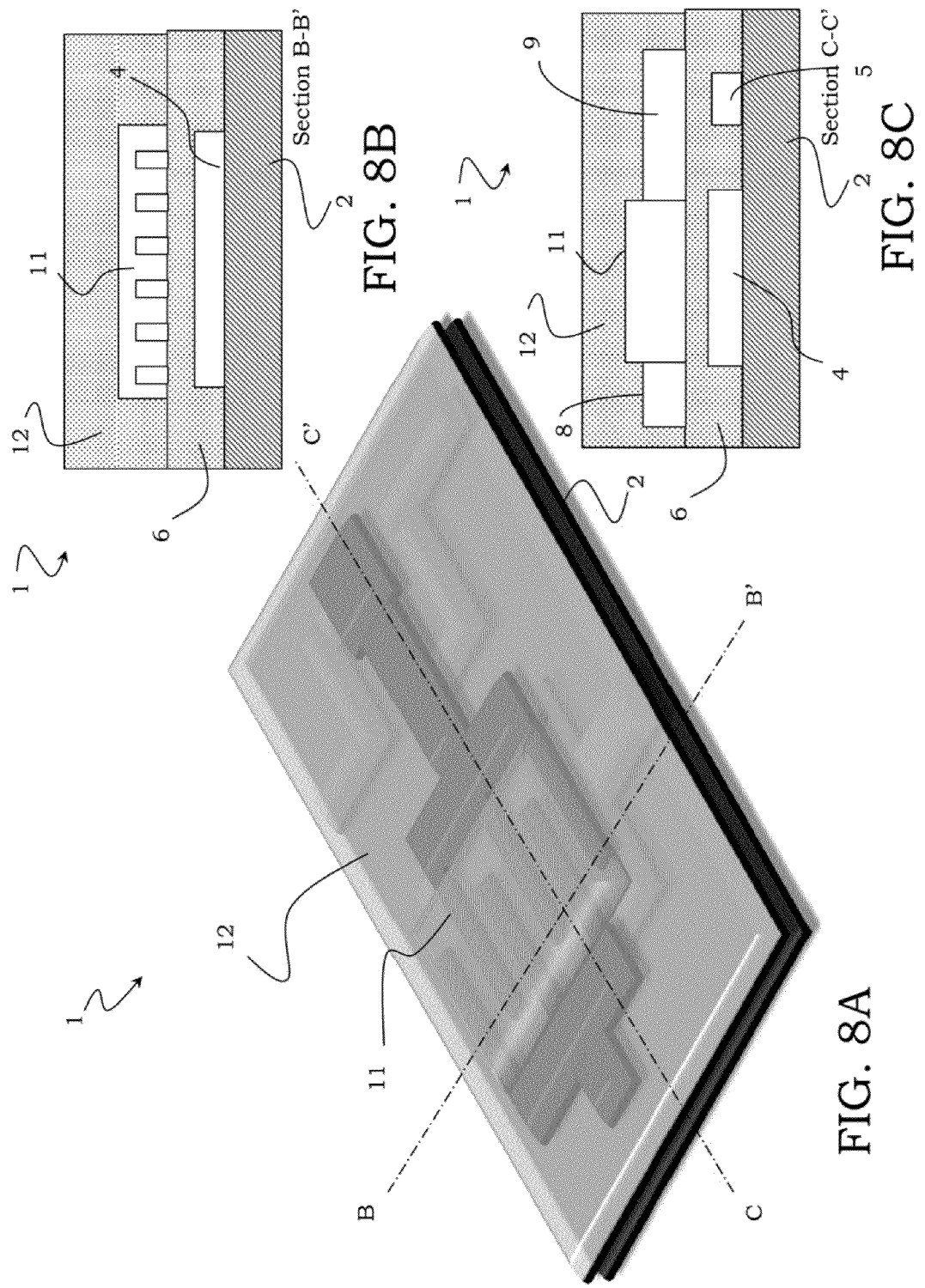

METHOD FOR MANUFACTURING A SENSOR DEVICE OF A GASEOUS SUBSTANCE OF INTEREST

BACKGROUND

1. Technical Field

The present disclosure relates to a method for manufacturing a sensor device of a gaseous substance of interest.

The disclosure also relates to a sensor device thus realized and to a sensing system comprising it.

The disclosure relates, even more in particular, but not exclusively, to a method for manufacturing a sensor device of a gaseous substance of interest of the type comprising at least one thin film transistor comprising a layer sensitive to gaseous substances, in particular toxic, such as for example nitrogen dioxide ($NO_2$), and the following description is made with reference to this field of application by way of illustration only.

2. Description of the Related Art

As it is well known, several inflammable, explosive, toxic gases are normally present in inhabited environments and, then, studying and realizing gas sensors for the sensing of these dangerous gases becomes of fundamental importance for the aim of reducing the environmental contamination and preserving human health.

Among gas sensors those comprising substances of organic nature or metallic-organic compounds able to detect the presence of one or more substances present in the environment in the gaseous form are well known, such as for example sensors of carbon monoxide (CO) or of oxygen ($O_2$). Several substances of organic nature and metallic-organic compounds are in fact known able to detect the presence or not of one or more substances present in the environment in the gaseous form through physical and chemical mechanisms of different nature and, then, able to perform, in general, sensing functions towards the same species of interest.

Among the various gas sensors, particular attention has been paid to semiconductor gas sensors by virtue of their low cost, of the small volumes, of the simple realization and of the high sensitivity. In particular, different oxides have been used as semiconductor materials for these semiconductor gas sensors, such as for example tin oxide ($SnO_2$), iron oxide ($Fe_2O_3$), manganese dioxide ($MnO_2$) and chromium monoxide (CrO).

Intense research and development activities are in particular aimed at the identification of suitable semiconductor materials and at the integration of the same in low cost electronic devices for the sensing of specific substances with a high selectivity and sensitivity degree towards the species of interest, in particular of those substances, considered toxic for humans beyond determined exposure levels, whose continuous monitoring plays, as said, a role of fundamental importance in all the environments frequented by humans, either domestic, or commercial, or public or industrial.

In this case, most of the materials having sensing functions towards this gaseous substance of interest comprise hybrid materials with a metallic component, in particular metallic oxides and/or metallic-organic compounds, based for example on Zinc (Zn), Indium (In), tin (Sn), Tungsten (W) and Molybdenum (Mo).

As it is well known, in fact, in the process of gas sensing executed by these sensors, the gas is adsorbed on the surface of the semiconductor material; in this way, according to the fact that the electronic affinity of the molecular gas is greater of smaller than the working function of the semiconductor material used, there is a transfer of electrons from the surface of the semiconductor material to the molecular gas or vice versa. This movement of electrons determines a variation of the electric resistance of the semiconductor material itself that, thus, may be related to the concentration and to the type of molecular gas detected.

It is also known that it is desirable for the gas sensing material to have a high sensitivity, a strong selectivity, a good stability, short response and recovery time. A semiconductor material having such characteristics is for example zinc oxide (ZnO), that has been, in fact, used in different known solutions of gas sensors. Zinc oxide (ZnO) is a semiconductor of the n type belonging to the family of the groups II-VI, having direct <<gap>> and distance between valence and conduction bands (Eg) equal to 3.37 eV. This characteristic, together with the high excitonic bond energy, i.e., the energy for separating electron and hole linked by colombian interaction, in the case of zinc oxide (ZnO) equal to about 60 meV, makes it suitable for electronic and/or optoelectronic applications, but also for applications within the sensorial domain.

In fact, zinc oxide (ZnO) has, besides the excellent electric characteristics, i.e., high mobility and wide band gap, low cost, non-toxicity, good environmental stability, high melting point and high transparency against the visible spectrum, with subsequent stability to the visible light with respect to other semiconductors with low band gap.

Gas sensors may be for example of the type with thick film or with thin film.

Gas sensors of the "thick film" type may be realized, for example, by means of the so called "screen printing" technology. In particular, according to this technology, a measuring electrode, a heating electrode and a sensitive paste containing a semiconductor material, a catalyst and an adhesive, are first printed on a substrate of the high temperature type, for example ceramic, and then sintered.

For gas sensors of the "thin film" type, a sensitive thin film is first spread on a ceramic substrate by means of vacuum thin film technology and, subsequently, on this thin film an electrode is formed.

All the gas sensors above described are of the type with two electrodes. They comprise in particular a positive electrode and a negative electrode, and a semiconductor, interposed between the two electrodes, for detecting the variation of electric resistance, and, then, of the electric current that flows between the two electrodes, according to the type and to the concentration of gas adsorbed on its surface.

At present, however, sensors with two electrodes are realized on little economic substrates that should sustain high temperature processes. Moreover, the measurement is based on the change of the electric resistance of a passive element with two terminals (such as a resistor) realized therein and, therefore, this measurement is not accurate enough in the cases of low concentrations of toxic gas to be detected.

Recent studies have led to solutions with gas sensors having three electrodes, wherein a gate electrode is added to the two electrodes, here with function of source and drain electrodes, realizing de facto a sensing transistor and optimizing the performances of the sensor itself, with particular reference to the sensitivity of the sensor for small amounts of substance to be detected.

An example of such a sensor is described in the US patent application with publication number US 2010/0050745, filed on Sep. 3, 2008 by National Formosa University. In this application a gas sensor is described that is realized with a Field Effect Transistor or FET based on nanowires of zinc oxide (ZnO) comprising a channel of charge carriers made of nanowires of zinc oxide (ZnO) comprised between the source and the drain of the transistor. The charge flow through the channel, and, thus, the electric resistance of the nanowires of zinc oxide (ZnO) is controlled by the gate terminal of the FET. Substantially, then, a small variation of the gate voltage may affect the electric current between source and drain.

Although advantageous under several aspects, this solution has several drawbacks. In fact, the realization process is complicated by the fact that the nanowires of zinc oxide (ZnO) are deposited before the realization of the source and drain electrodes, involving high temperature process steps, non-compatible with the cheaper and more flexible typologies of substrates such as for example plastic substrates. Moreover, the FET described in this solution comprises a metallic layer suitable for realizing a heating element. Finally, the FET described is not specifically designed for the sensing in the air of toxic gaseous substances, such as for example nitrogen dioxide ($NO_2$).

In particular, it is known that the presence of nitrogen dioxide ($NO_2$) is tolerated in amounts not larger than 3 ppm for an exposure time not higher than 8 hours, or in amounts not larger than 5 ppm for an exposure time not higher than 15 min.

Thus, it becomes of fundamental importance, in the microelectronics industry, to favor the production and the marketing of systems, such as exactly the gas sensors, for the sensing and the monitoring of gaseous substances, in particular dangerous gases, to significantly reduce the costs of the single elements constituting them and to increase their reliability, the sensitivity, the specificity, the stability and the mechanical strength.

More in particular, the need is felt of realizing low cost sensors of nitrogen dioxide ($NO_2$) able to detect minimal amounts of this gas, for example of the order of ~1 ppm.

BRIEF SUMMARY

One embodiment of the present disclosure is a method for manufacturing a sensor device of a gaseous substance of interest, having such structural and functional characteristics as to obtain a high sensitivity of the sensor with low cost manufacturing processes overcoming the limits and/or the drawbacks still limiting the gas sensors realized according to the prior art.

One embodiment of the present disclosure uses, as sensor element of a gaseous substance of interest, a thin film transistor (TFT) in "bottom gate" configuration, with a semiconductor channel based on a thin film of zinc (ZnO) serving as sensitive element a gaseous substance being present, in particular toxic, such as for example the compounds of the nitrogen oxide, or NOx and more in particular the nitrogen dioxide ($NO_2$).

One embodiment of the present disclosure is based on the idea of exploiting the operation mechanism of a sensor device as above indicated, for realizing a simple and efficient sensing system comprising a sensor device thus realized and a second device serving as active load.

One embodiment of the present disclosure is a manufacturing method of at least a sensor device of a gaseous substance of interest integrated on a substrate comprising at least one thin film transistor in turn comprising a source electrode, a drain electrode and a gate electrode as well as at least one sensitive element to said gaseous substance of interest, said method comprising the steps of:

preparing of said substrate and forming thereon a first metallic layer;

defining and patterning said first metallic layer for realizing said gate electrode;

depositing a layer of dielectric material above said gate electrode; depositing a second metallic layer above said layer of dielectric material, defining and patterning of said second metallic layer for realizing said source electrode and said drain electrode;

forming said at least one sensitive element by means of filling of a channel region of said thin film transistor with an active layer sensitive to said gaseous substance of interest.

More in particular, the disclosure comprises the following supplementary and optional characteristics, taken singularly or if need be in combination.

According to an aspect of the disclosure, said filling step of said channel region may realize as active layer one thin layer of zinc oxide (ZnO) or of a derivative thereof.

According to another aspect of the disclosure, said filling step of said channel region may realize as active layer a thin layer comprising at least one among zinc oxide (ZnO), its ternary derivatives, such as zinc oxide and antimonium (AZO) and its quaternary derivatives, such as zinc oxide, indium and gallium (GIZO).

According to the above aspect of the disclosure, for the purpose of more clarity, such ZnO derivatives, includes any material composites made by embedding ZnO nanoparticles in a polymer or polymer nanofibers such as, but not limited to, polyaniline(PANI) and polypyrrole (Ppy).

According to another aspect of the disclosure, said filling step of said channel region may realize as active layer a thin layer comprising a polymer such as PANI and Ppy without including ZnO nanoparticles.

According to an aspect of the disclosure, said filling step of said channel region may be realized downstream of said definition step of said source electrode and of said drain electrode.

According to another aspect of the disclosure, said depositing step of a layer of dielectric material above said gate electrode deposits a layer of an organic substance or of a metallic-organic compound.

Furthermore, according to an aspect of the disclosure, said substrate may be of the insulating rigid insulating rigid type.

According to another aspect of the disclosure, said substrate may be covered by a layer comprised in the group constituted by:

silicon oxide;
glass;
quartz.

Moreover, according to a further aspect of the disclosure, said substrate may be of the plastic type.

In particular, according to this aspect of the disclosure, said substrate may be a film of naphthalate polyester (PEN) laminated on a rigid support by means of a suitable thermal release adhesive paste for realizing said substrate.

Always according to this aspect of the disclosure, said method may comprise, at the end of all the process steps of said method, a final step of delamination of said film of naphthalate polyester (PEN) from said rigid support.

Furthermore, according to an aspect of the disclosure, said defining and patterning steps of said first and second metallic layer may comprise a selective photolithographic step.

According to another aspect of the disclosure, said formation step of said first metallic layer comprises, in succession, the steps of:

executing on said substrate a preliminary treatment with oxygen plasma; and depositing at least one metallic layer.

According to this aspect of the disclosure, said at least one metallic layer may be chosen in the group constituted by:

gold;
a double layer made of a transition metal and by a gold layer;
a noble metal.

According to another aspect of the disclosure, said depositing step of said layer of dielectric material may be followed by a step of surface treatment with oxygen plasma.

Further, according to an aspect of the disclosure, said defining and patterning step of said first metallic layer may also realize a first plurality of circuit interconnections.

According to an aspect of the disclosure, said defining and patterning step of said second metallic layer may also realize a second plurality of circuit interconnections.

In particular, according to this aspect of the disclosure, the method may further comprise a step of forming holes through said layer of dielectric material, suitable for establishing conductive paths between said first plurality of circuit interconnections and said second plurality of circuit interconnections.

According to another aspect of the disclosure, said step of forming said at least one sensitive element may comprise a deposition step chosen in the group made of:
depositing said thin layer of zinc oxide (ZnO) or of a derivative thereof with low temperature, through sputtering;
depositing said thin layer of zinc oxide (ZnO) or of a derivative thereof with low temperature, through RF magnetron sputtering;
deposition through solution of a precursor of zinc oxide (ZnO) or of a derivative thereof and successive thermal activation for the formation of said thin layer of zinc oxide (ZnO) or of a derivative thereof;
deposition through solution of a mixture containing a precursor of zinc oxide (ZnO) or of a derivative thereof suitably dispersed in a polymeric matrix, followed by a step of thermal activation for the formation of said thin layer of zinc oxide (ZnO) or of a derivative thereof.

According to an aspect of the disclosure, the method may further comprise, further to said formation step of said at least one sensitive element, an encapsulation step of said sensor device by means of deposition of a dielectric layer above said thin film transistor.

Moreover, according to another aspect of the disclosure, said encapsulation step may further comprise an opening step of said dielectric layer in correspondence with said sensitive element of said thin film transistor so as to directly expose a sensitive channel area of said thin film transistor to said gaseous substance of interest.

According to an aspect of the disclosure, said encapsulation step comprises a deposition step of a dielectric layer of permeable material by said gaseous substance of interest, to allow the transport of said gaseous substance up to the channel sensitive area of said thin film transistor through said dielectric layer.

In particular, according to this aspect of the disclosure, the possibility will be appreciated of controlling in an excellent way the selectivity of said sensor device in the sensing of said gaseous substance of interest with respect to other substances that cannot be subjected to being transported through said dielectric layer used in said encapsulation step.

One embodiment of the present disclosure is a sensor device of a gaseous substance of interest integrated on a substrate and comprising at least one thin film transistor in turn comprising a source electrode, a drain electrode and a gate electrode as well as at least one sensitive element that comprises an active layer sensitive to said gaseous substance of interest for realizing a channel region of said thin film transistor, in turn including a layer of dielectric material, that serves as gate dielectric.

According to an aspect of the disclosure, said active layer may comprise a thin layer of zinc oxide (ZnO) or of a derivative thereof.

According to another aspect of the disclosure, said active layer may be a thin layer comprising at least one among zinc oxide (ZnO), its ternary derivatives and its quaternary derivatives.

According to the above aspect of the disclosure, for the purpose of more clarity, such ZnO derivatives, includes any material composites made by embedding ZnO nanoparticles in a polymer or polymer nanofibers such as, but not limited to, polyaniline(PANI) and polypyrrole (Ppy).

According to another aspect of the disclosure, said active layer may be a thin layer comprising a polymer such as PANI and Ppy without including ZnO nanoparticles.

According to a further aspect of the disclosure, said layer of dielectric material is a layer of an organic substance or of a metallic-organic compound.

One embodiment of the present disclosure is a sensing system of a gaseous substance of interest inserted between a first and a second voltage reference and connected to a generator of an input voltage, in turn connected to said second voltage reference, said sensing system having an output terminal suitable for supplying a voltage and at least one first sensing transistor and one second load transistor, inserted, in series to each other, between said first and second voltage reference and interconnected in correspondence with said output terminal, said first sensing transistor being a thin film transistor comprising a semiconductor channel realized by an active layer sensitive to said gaseous substance of interest and able to vary the threshold voltage of said first sensing transistor according to a charge amount entrapped therein as effect of the exposure to said gaseous substance to be detected.

According to an aspect of the disclosure, said first sensing transistor and said second load transistor may form an inverter of the CMOS type and have respective control terminals connected to each other and to said generator of an input voltage.

According to this aspect of the disclosure, said second load transistor may be a transistor of the p type serving a active load.

According to another aspect of the disclosure, said CMOS inverter may transform an electric current generated by said first sensing transistor into a voltage signal on said output terminal of said sensing system.

Further, according to an aspect of the disclosure, said active layer of said first sensing transistor may comprise a thin layer of zinc oxide (ZnO) of a derivative thereof.

The characteristics and the advantages of various embodiments of the method and of the device according to the disclosure will be apparent from the following description of an embodiment thereof given by way of indicative and non-limiting example with reference to the annexed drawings.

BRIEF DESCRIPTION OF THE SEVERAL VIEWS OF THE DRAWINGS

In these drawings:
FIGS. 1A, 1B, 2A, 2B, 2C, 3A, 3B, 3C, 4A, 4B, 4C, 5A, 5B, 5C, 6A, 6B, 6C, 7A, 7B, 7C, 8A, 8B and 8C are schematic views, three-dimensional and in section, along the axes B-B' and C-C', respectively, of a portion of substrate, rigid or flexible, during successive steps of a manufacturing method of a sensor device of a gaseous substance of interest, according to the disclosure;

DETAILED DESCRIPTION

Figures 9A, 9B:
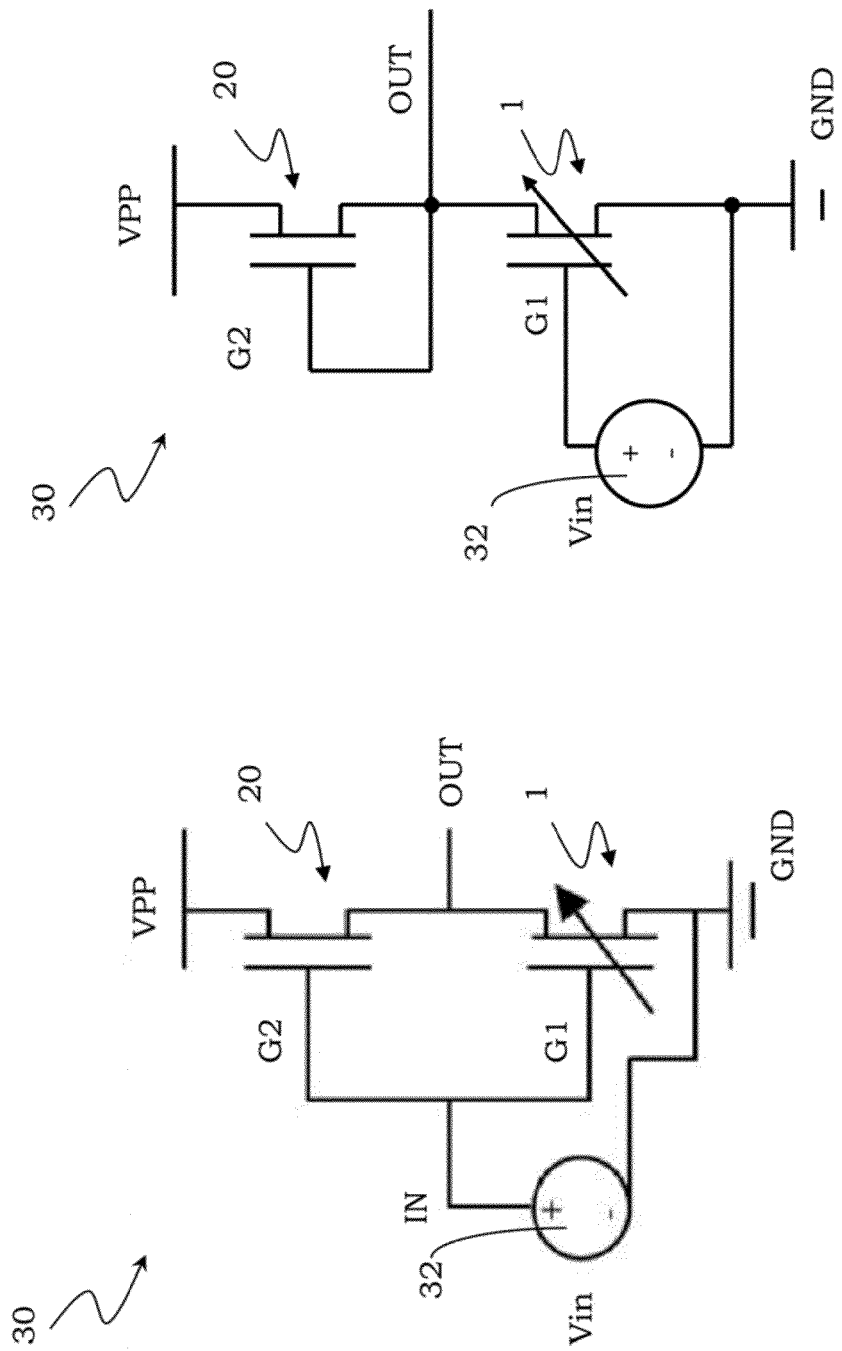
FIGS. 9A and 9B are circuit schematic views of embodiments of a sensing system of a gaseous substance of interest, according to the disclosure.

With reference to these figures, a method is described for manufacturing a sensor device of a gaseous substance of interest, in particular toxic, comprising at least one thin film transistor (TFT) in "bottom gate" configuration, with a semiconductor channel realized by a thin film of active material, such as zinc oxide (ZnO), serving as sensitive element for sensing the presence of a gaseous substance of interest, such as for example the compounds of the nitrogen oxide or NOx or more in particular nitrogen dioxide ($NO_2$).

In particular, hereafter the steps are described of a method for manufacturing a sensor device 1 of a gaseous substance of interest, according to the disclosure, in particular comprising a thin film transistor.

In particular, the method comprises an initial step of preparation of a substrate 2, as shown in FIGS. 1A, 1B and 1C.

According to an aspect of the disclosure, the substrate 2 is of the insulating rigid type, for example silicon, and is covered by a layer of silicon oxide, or, alternatively, glass, or quartz.

Alternatively, the substrate 2 is a plastic substrate, for example a film of polyester like naphthalate polyester, or PEN, which is preferably laminated on a support, or "carrier", of silicon through a suitable thermal release adhesive paste. In this way it is possible to use standard lithography techniques for the definition of contacts and patterning of successive functional layers.

In particular, the film of naphthalate polyester (PEN) is laminated, temporarily, on a rigid support, in particular of silicon or glass, through a suitable thermal release adhesive paste for realizing the substrate 2. This film of naphthalate polyester (PEN) is maintained on the rigid substrate, for the whole duration of the steps of the manufacturing method of the sensor device 1 and then, subsequently, delaminated from the rigid support for obtaining a final device, mechanically flexible and foldable, for adapting itself to surfaces of various type and form according to the applicative needs.

According to an aspect of the disclosure, in a successive step, a first metallic layer 3 is formed on the substrate 2. In particular, this step of formation of the first metallic layer 3 comprises a preliminary treatment with oxygen plasma and to a successive vapor deposition, or, alternatively, through a low temperature "sputtering" process, of one or more metallic layers, for example gold or a double layer made of a transition metal, for example titanium, chromium or nickel, and of a gold layer. Alternatively, other conductive materials may be used, for example noble metals, such as silver or platinum, or copper. The surface treatment of the substrate 2 by means of oxygen plasma in particular facilitates or promotes the adhesion of the first metallic layer 3.

The method then comprises a defining and patterning step of the first metallic layer 3 for realizing at least one contact of the thin film transistor 1, in particular a gate contact 4, as shown in the FIGS. 2A, 2B and 2C, FIGS. 2B and 2C being sections of FIG. 2A along the axes B-B' and C-C', respectively.

This defining and patterning step uses in particular a photolithographic technique, based on the depositing of a photoresist layer on the metallic layer 3, definition through a photolithographic mask and selective development of the photoresist so as to open some regions of the metallic layer 3 to be exposed to one or more chemical etching solutions suitable for removing them. Thus, a determined "patterning" is obtained of the metallic layer 3 useful for the definition of this contact, in particular a gate electrode 4 of the thin film transistor 1; a plurality 5 of circuit interconnections is also defined in the first metallic layer 3.

According to another aspect of the disclosure, other patterning techniques may be used, for example a lithography for "lift-off".

Further, according to an aspect of the disclosure, a heating element, not shown in the figure, may be integrated above the substrate 2.

The method then comprises a further deposition step of a layer 6 of dielectric material, serving as gate dielectric, as shown in the FIGS. 3A, 3B and 3C, FIGS. 3B and 3C being sections of FIG. 3A along the axes B-B' and C-C', respectively. According to an aspect of the disclosure, this further deposition step is realized through "spin coating". Alternatively, the layer 6 of dielectric material is formed by vapor deposition.

According to an aspect of the disclosure, the layer 6 of dielectric material comprises an organic substance or a metallic-organic compound.

According to one embodiment of the disclosure, the method comprises, after the deposition step of the layer 6 of dielectric material, a surface treatment step of this layer, for example a mild treatment with oxygen plasma, for activating it and making it suitable for the adhesion with functional layers subsequently formed. Such a surface treatment step is optional.

The method also comprises a step of realization of source and drain interdigitated electrodes of the thin film transistor 1. In particular, this realization step comprises a deposition step of a second metallic layer 7 above the layer 6 of dielectric material, as shown in the FIGS. 4A, 4B and 4C, FIGS. 4B and 4C being sections of FIG. 4A along the axes B-B' and C-C', respectively, as well as a successive photolithography step, suitable for defining a source electrode 8, drain electrode 9, preferably interdigitated as shown, and a plurality 10 of interconnections of second level, as shown in the FIGS. 5A, 5B and 5C, FIGS. 5B and 5C being sections of FIG. 5A along the axes B-B' and C-C', respectively.

More in particular, the deposition step of a second metallic layer 7 may comprise a vapor deposition, or, alternatively, a low temperature "sputtering" process, of one or more metallic layers, in a way similar to the formation step of the first metallic layer 3, as indicated above.

Similarly, the photolithography step for realizing the source and drain electrodes, 8 and 9, as well as the plurality 10 of interconnections of second level may comprise the deposition of a photoresist layer, the definition through a photolithographic mask and selective development of the photoresist and the exposure to one or more chemical etching solutions, as it occurs for the patterning of the first metallic layer 3.

According to one embodiment of the disclosure, "holes" may be realized through the layer 6 of dielectric material, so as to establish conductive paths 13 between the plurality 5 of circuit interconnections realized in the first metallic layer 3 and the plurality 10 of interconnections of second level realized in the second metallic layer 7. These holes may be realized through lithographic techniques or, alternatively, techniques of imprinting with molds, of "inkjet printing" of the solvent for the dielectric material. The conductive paths 13 may be formed by portions of the second metallic layer 7 being deposited in the holes or by depositing one or more other conductive layers in the holes and planarizing the one or more other conductive layers to leave only portions of the one or more conductive layers forming the conductive paths 13.

The method also comprises a step of formation of a sensitive element 11 that is sensitive to a gaseous substance of interest being present, in particular toxic. More in particular, the sensitive element 11 is formed by filling in the channel of the thin film transistor 1 with an active layer, such as a semiconductor layer of zinc oxide (ZnO) or its ternary derivatives, for example indium zinc oxide (IZO), zinc oxide and antimonium (AZO), etc., and quaternary derivatives, for example zinc oxide, indium and gallium (GIZO), etc. Such ZnO derivatives, includes any materials composites made by embedding ZnO nanoparticles in a polymer or polymer nanofibers such as, but not limited to, PolyAniline(PANI) and Polypyrrole (Ppy).

According to another embodiment, said active layer may be a thin layer comprising a polymer such as PANI and Ppy without including ZnO nanoparticles.

This formation step comprises for example a low temperature deposition step of zinc oxide (ZnO), in particular through sputtering, as it is well known according to the physical phenomenon in which positive ions of a gas, usually of argon (Ar+), are accelerated by means of a potential gradient so as to bombard a cathode (material to be deposited), exactly defined target. Since the ions give their momentum to the atoms on the surface of the target, these latter are extracted from the target and pushed towards the substrate, where they are deposited in the form of a thin film.

It is suitable to remind that the zinc oxide (ZnO) deposited through sputtering preserves excellent optical properties and has a polycrystalline structure, i.e., a structure with a localized crystalline periodicity, strongly oriented, the grains in fact grow following the axes perpendicular to the surface of the substrate, and each single grain shows the hexagonal symmetry typical of the bulk crystal, also for depositions on amorphous substrate.

By means of the deposition through sputtering it is also possible to modify some properties of the film of material obtained, controlling the progress of the refraction index of the material by varying the amount of oxygen ($O_2$) in the deposition chamber [as described by Gioffrè et al., Superlattices and Microstructures, 42 (2007) 85-88], which is incorporated by reference herein in its entirety, or by modifying the electric properties thanks to cosputtering techniques for doping the film of material obtained.

This deposition technique has, finally, the advantage of having the possibility to be used for depositing thin films of zinc oxide (ZnO) on each type of substrate and at low temperatures, although allowing to obtain a material having good structural characteristics.

According to an aspect of the disclosure, this low temperature deposition step of zinc oxide (ZnO) is carried out through RF magnetron sputtering. This known embodiment allows the local formation in situ of a film of zinc oxide with excellent optical properties and a structure of the polycrystalline type.

This step allows, moreover, to realize binary, ternary and quaternary oxides among which for example zinc oxide (ZnO), zinc oxide and Antimonium (AZO), zinc oxide and Indium (IZO), zinc oxide, Indium and Gallium (GIZO), etc. with the same process characteristics and having the possibility to be controlled at temperatures compatible with plastic substrates. The disadvantage stays in the possibility that the gate dielectric may be partially deteriorated as effect of the ionic bombardment whereon the sputtering technique itself is based for extracting the ions desired by the specific target.

Alternatively, a deposition is carried out through solution of a precursor and successive thermal activation for the formation of the oxide as active material.

According to a further embodiment of the disclosure, the deposition of zinc oxide (ZnO) or of a derivative thereof is carried out starting from a solution containing a precursor of the zinc oxide (ZnO) or of a derivative thereof suitably dispersed in a polymeric matrix, for example acetate of Zinc in methoxyethanol or other possible precursors, having the function of controlling and adapting its formulation for making the active material suitable for being processed through solution. With this type of deposition, it is possible that the solution is deposited only in the active area of interest, for example through spin coating, inkjet printing, flexo printing, gravure printing, screen printing, solution casting, spray coating, or aerosol jet printing. This technique has the advantage of a better compatibility with the underlying layers of the transistor where a solvent is selected orthogonal to the solvent of the material used as gate dielectric, i.e., that does not dissolve it. The deposition step of the precursor is then followed by a thermal activation step or "annealing" for promoting the decomposition of the precursor and the formation of the zinc oxide or of other compounds deriving therefrom.

During the annealing step, the precursor decomposes in zinc oxide (ZnO) and fills in the gaps in the channel region of the transistor. Transistors realized with this technique reach good performances with mobility of 1.2 $cm^2$ $V^{-1}$ $s^{-1}$ and a high ration On/Off ($10^5$-$10^6$). This type of approach also allows the use of plastic substrates.

It is to be noted that in this case the heating profile has a crucial impact on the crystalline orientation of zinc oxide (ZnO) which influences the properties of the thin film transistor 1 thus obtained.

Alternatively, it is possible to realize the active material in the form of polymer-based compound containing a sufficient amount of nanoparticles of zinc oxide (ZnO) or of its ternary or quaternary compounds in the form of nanorods, nanowires or other forms of nanoparticles suitably functionalized for being dispersed in the polymeric matrix of the compound and, together, formulated for ensuring its deposition through solution, with the various techniques above indicated. For example, the polymer matrix may be of PANI, Ppy, or other suitable polymer.

Alternatively, the active layer can be a thin layer of ZnO nanoparticles interspersed with other nanoparticles, such as PANI nanofibers. Also, the active layer can be a layer of PANI nanofibers, Ppy, or other suitable polymers without any ZnO nanoparticles.

Any of the above-mentioned active materials can be deposited using a solution in water or other solvent of the various active materials, including ZnO nanoparticles, PANI nanofibers, monomers, etc, or suitable precursors of those materials. Any of the above-mentioned deposition methods can be employed.

In FIGS. 6A, 6B and 6C, FIGS. 6B and 6C being sections of FIG. 6A along the axes B-B' and C-C', respectively, the thin film transistor 1 is thus shown comprising a sensitive element 11 formed by a layer of zinc oxide (ZnO), deposited on a region comprising the source electrode 8 and the drain electrode 9, serving as channel of the transistor itself, as realized according to the disclosure.

In this way a thin film transistor is realized in bottom-gate, bottom-contact configuration.

More in particular, according to an aspect of the disclosure, the thin film transistor 1 comprises at least one layer 6 of dielectric material, serving as gate dielectric.

According to another aspect of the disclosure, after the step of formation of the sensitive element 11, the method comprises the step of encapsulation of the device thus obtained in the areas outside the active area constituted exactly by the sensitive element 11. As shown in FIGS. 7A, 7B and 7C, FIGS. 7B and 7C being sections of FIG. 7A along the axes B-B' and C-C', respectively, this step of encapsulation comprises a deposition step of a dielectric layer 12 with function of encapsulating element, also called passivation layer, and a step of forming an opening 14 in this dielectric layer 12, during or after its deposition step, in correspondence with the active area of the thin film transistor 1 so as to delimit the sensitive element 11. In this way, the sensitive element 11 is able to carry out a direct sensing of the gaseous substance of interest.

Alternatively, as shown in FIGS. 8A, 8B and 8C, FIGS. 8B and 8C being sections of FIG. 8A along the axes B-B' and C-C', respectively, this encapsulation step provides a deposition of the dielectric layer 12 with function of encapsulating element, or passivation layer, on the whole sensor device 1, the dielectric layer 12 with function of encapsulating element. In particular, the material realizing the dielectric layer 12 may be selected so as to have function of permeable membrane in a selective way to the gaseous substance of interest, with the aim of increasing the selectivity of the sensor device with respect to the gaseous substance of interest, exactly.

The disclosure also relates to a sensing system of a gaseous substance of interest, in particular toxic, of the type shown in FIG. 9A, globally indicated with 30.

In particular, the sensing system 30 comprises a first gas sensor device 1, in particular a thin film transistor of the type above described, also called sensing transistor 1 and a second device 20, in particular a transistor of the p type serving as active load, also called load transistor 20. More in particular, the sensing transistor 1 is a thin film transistor with channel n in "bottom gate" configuration, with a semiconductor channel comprising a thin film of zinc oxide (ZnO), serving as gas sensor and varying the threshold voltage of the transistor itself according to the amount of charge entrapped as effect of the exposure to the gaseous substance to be sensed, in particular nitrogen dioxide ($NO_2$).

The sensing transistor 1 and the load transistor 20 are positioned, in series to each other, between first and second voltage reference terminals, respectively of supply VPP and ground GND, are interconnected in correspondence with an output terminal OUT of the sensing system 30, and have respective gate terminals, G1 and G2, connected to an input terminal IN, in turn connected to the ground reference GND by a voltage generator 32 configured to generate an input voltage Vin. The sensing transistor 1 and the load transistor 20 thus form a circuit stage with simple inverter, in particular in CMOS technology, suitable for transforming the electric current generated by the sensing transistor 1 thanks to the modification of its threshold voltage as effect of the exposure to the gaseous substance to be sensed in a voltage signal.

It is to be noted that the load transistor 20 may be manufactured in the same low cost technological platform of the sensing transistor 1.

Alternatively, the load transistor 20 may be of the same type as the sensing transistor 1, diode-connected to form an active load according to a configuration NMOS, as schematically shown in FIG. 9B.

In this case, the sensing transistor 1 and the load transistor 20 are inserted, in series to each other, between a first and a second voltage reference, respectively of supply VPP and ground GND, and are interconnected in correspondence with an output terminal OUT of the sensing system 30.

The sensing transistor 1 has a gate terminal G1 connected to the ground reference GND by the voltage generator 32, while the load transistor 20 has a gate terminal G2 diode-connected to its own source terminal and to the output terminal OUT of the sensing system 30.

In particular, the sensing transistor 1 and the load transistor 20 are totally encapsulated so as not to vary the response of the sensing system 30 to the gaseous substance of interest being present.

Figure 10A:
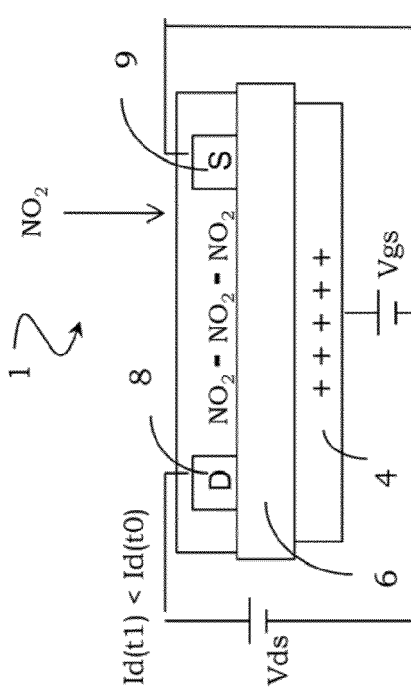
FIGS. 10A-10C are respective schematic section views of a sensor device of a gaseous substance of interest during successive steps of its operation, according to the disclosure.
Figure 10B:
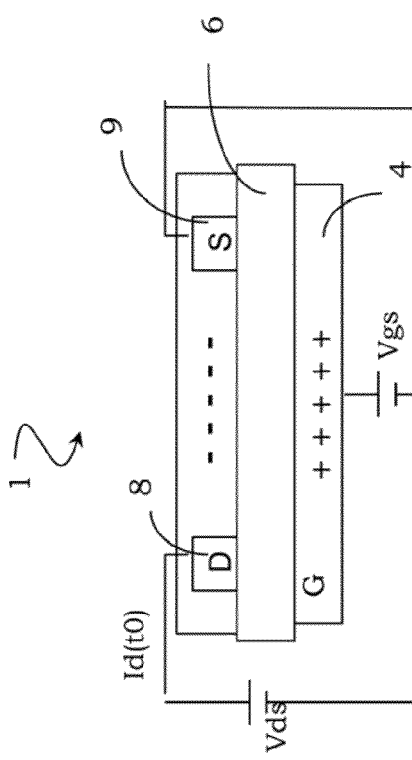
Figure 10C:
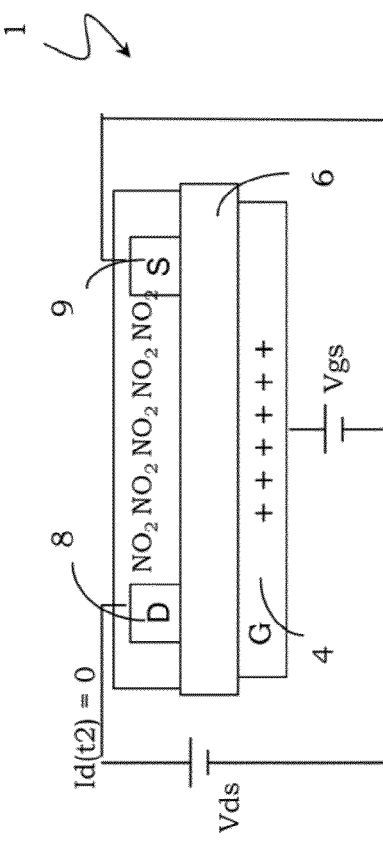

FIGS. 10A-10C show the sensing transistor 1 during successive steps of its operation, in case of sensing of nitrogen dioxide ($NO_2$) as gaseous substance of interest. In particular, when the sensing system 30 is supplied by the input voltage Vin, a voltage Vds is established between the source electrode 8 and the drain one 9 of the sensing transistor 1, while on the gate electrode 4 a voltage Vgs is established, whose value induces a modulation of the current in the sensitive element 11 formed by the layer of zinc oxide (ZnO). In fact, in the channel of zinc oxide (ZnO) a channel of carriers is created, whose electric resistance varies with the voltage associated therewith and applied thereto until reaching a saturation value. The electric characteristics of such a transistor are described by two equations:

$$I_{DS} = (W/L) \cdot \mu \cdot C_{ox} \cdot (V_{GS} - V_T) V_{DS} \text{ for } V_{DS} < V_{GS} - V_T \text{ (linear region)};$$

$$I_{DS} = (W/2L) \cdot \mu C_{ox} \cdot (V_{GS} - V_T)^2 \text{ for } V_{DS} > V_{GS} - V_T \text{ (saturation)};$$

where $\mu$ is the mobility of the minority carrier, $C_{ox}$ the gate capacitance, W and L the channel width and length, $V_T$ the threshold voltage for the turn-on of the transistor.

Therefore, the drain current Id in the channel of zinc oxide (ZnO), at the instant of time t=0, when there is no gaseous substance of interest in the environment, has a certain value Id(t0), which decreases when the channel of zinc oxide (ZnO) absorbs the first molecules of gas, for example $NO_2$. In substance, at an instant of time t1, after which the absorption of gas has occurred, the value of current Id(t1) become lower than Id(t0). When the concentration of absorbed gas increases, the current Id decreases until it is nullified at an instant of time t2.

Figure 11:
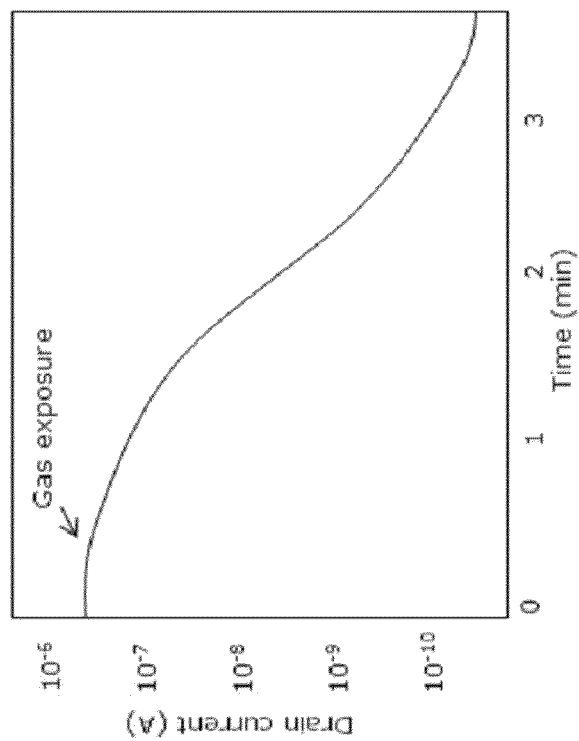
FIG. 11 shows the progress of the drain current of the sensing system according to the disclosure as a function of the time, a gaseous substance of interest being present.

By way of example, FIG. 11 shows the progress of the drain current Id as a function of the time, obtained with the sensing system 30 according to the disclosure.

Figure 12:
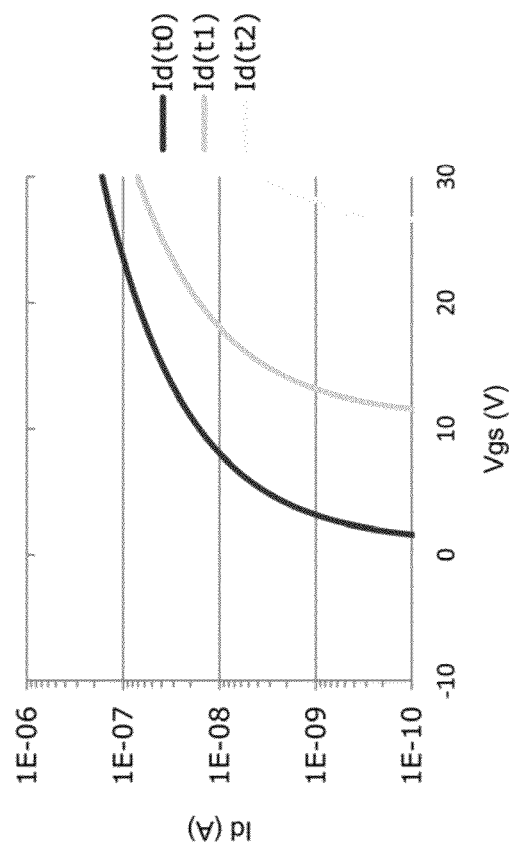
FIG. 12 shows a diagram of the drain current of the sensing system according to the disclosure during successive steps of its operation.

Consequently, the threshold voltage $V_{TH}$ of the gate voltage-source Vgs of the sensing transistor 1 is shifted according to the amount of charge entrapped in the channel of zinc oxide (ZnO) as effect of the absorption of the molecules of NOx, which depends on the amount of substance present in the air and on the exposure time, determining the modulation of the drain current flowing in both the transistors 1 and 20. FIG. 12 shows a diagram of the drain current Id from the instant of time t0 to the instant of time t2, wherefrom it is derived how the drain-source voltage Vds of the transistors 1 and 20 quickly varies according to the drain current. Therefore, the value of the output voltage Vout of the inverter circuit formed by transistors 1 and 20 supplies direct information on the concentration of gas the sensing system 30 has been exposed to.

More in particular, according to an aspect of the disclosure, the value of the output voltage Vout may take two levels, respectively corresponding to the presence or not of the gaseous substance of interest, assumed noxious, in smaller or bigger amounts than the minimum value of exposure to the substance to be sensed.

Advantageously, the method according to the disclosure may be applied to matrixes of sensors, in particular to a sensing system 30 comprising a plurality of sensing transistors 1 organized in matrix.

Furthermore, the method may be used for integrating a plurality of sensors, each specific for a specific family of substances, in a same sensing system 30. In this way, it is possible to realize a so called "electronic nose" useful for applications in the chemical and biological field.

It is also possible to realize matrixes of sensors connected to each other that sense the gaseous substance each for a different exposure value.

In conclusion, the method according to the disclosure allows to realize a sensor of gaseous substances, in particular toxic such as the nitrogen dioxide ($NO_2$), simple and low cost and with scalable industrial processes.

More in particular, advantageously according to the disclosure, it is possible to use such a sensor for monitoring the levels of nitrogen dioxide ($NO_2$), one of the most diffused toxic gaseous substances that invalidates the quality of the air and whose evolution is constantly monitored within the European and national domains.

The deposition process used for realizing the active channel based on zinc oxide (ZnO) of the thin film transistor in bottom gate, bottom contact configuration to be used as sensor of nitrogen dioxide ($NO_2$) according to the disclosure it is in fact compatible with the low cost integration processes typical of the 'printed electronics' platform and with the use of polymeric substrates.

The method according to the disclosure thus allows to provide, at sustainable costs, sensors of nitrogen dioxide ($NO_2$) with the required levels of sensitivity and reliability, the implementation and the diffusion of systems and sensors networks distributed certainly favoring the improvement of the amount of the life.

Moreover, the method allows to realize a sensing system that may be integrated with the same process and in particular on plastic substrate.

Obviously a skilled in the art, with the aim of meeting contingent and specific needs, will be allowed to introduce several modifications in the method and the system above described, all within the scope of the disclosure.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
   manufacturing a sensor device configured to sense a gaseous substance and including a thin film transistor that includes a source electrode, a drain electrode, a gate electrode; and a sensitive element sensitive to said gaseous substance, said manufacturing including:
   forming a first metallic layer on a substrate;
   forming said gate electrode by defining and patterning said first metallic layer;
   depositing a first dielectric layer above said gate electrode;
   depositing a second metallic layer above said first dielectric layer;
   forming the source and drain electrodes by defining and patterning said second metallic layer; and
   forming said sensitive element by filling a channel region of said thin film transistor with an active layer sensitive to said gaseous substance; and
   encapsulating said sensor device by depositing a second dielectric layer above said entire thin film transistor, wherein said second dielectric layer is a material that is permeable by said gaseous substance so as to allow the transport of said gaseous substance to said sensitive element through said second dielectric layer.

2. A method according to claim 1, wherein said filling said channel region forms the active layer and includes a layer of zinc oxide or a derivative thereof.

3. A method according to claim 1, wherein said filling includes forming the active layer of at least one among zinc oxide, ternary derivatives of zinc oxide, and quaternary derivatives of zinc oxide.

4. A method according to claim 1, wherein said filling is performed after defining said source electrode and said drain electrode.

5. A method according to claim 1, wherein said substrate is silicon covered by a layer that includes at least one of:
   silicon oxide;
   glass; and
   quartz.

6. A method according to claim 1, comprising treating said substrate with oxygen plasma prior to depositing the first metallic layer.

7. A method according to claim 1, wherein forming the sensitive element comprises one of the following:
   depositing a thin layer of zinc oxide or of a derivative thereof with low temperature, via sputtering;
   depositing a thin layer of zinc oxide or of a derivative thereof with low temperature, via RF magnetron sputtering;
   forming thin layer of zinc oxide or of a derivative thereof by depositing a solution of a precursor of zinc oxide or of a derivative thereof and thermally activating the solution; and
   forming a thin layer of zinc oxide or of a derivative thereof by depositing solution containing a precursor of zinc oxide or of a derivative thereof suitably dispersed in a polymeric matrix, and thermally activating the solution.

8. The method according to claim 1, wherein before forming a first metallic layer on the substrate, the method further comprises forming the substrate by depositing a film of naphthalate polyester on a rigid support using a thermal release adhesive paste.

9. A method comprising:
   manufacturing a sensor device configured to sense a gaseous substance and including a thin film transistor that includes a source electrode, a drain electrode, a gate electrode, and a sensitive element sensitive to said gaseous substance, said manufacturing including:

forming a substrate by depositing a film of naphthalate polyester on a rigid support using a thermal release adhesive paste;
forming a first metallic layer on the substrate;
forming said gate electrode by defining and patterning said first metallic layer;
depositing a first dielectric layer above said gate electrode;
depositing a second metallic layer above said first dielectric layer;
forming the source and drain electrodes by defining and patterning said second metallic layer; and
forming said sensitive element by filling a channel region of said thin film transistor with an active layer sensitive to said gaseous substance.

10. A method according to claim 9, comprising, after forming the sensor device, delaminating said film of naphthalate polyester from said rigid support.

11. A method comprising:
manufacturing a sensor device configured to sense a gaseous substance and including a thin film transistor that includes a source electrode, a drain electrode, a gate electrode, and a sensitive element sensitive to said gaseous substance, said manufacturing including:
forming a first metallic layer on the substrate;
forming said gate electrode by defining and patterning said first metallic layer;
depositing a first dielectric layer above said gate electrode;
treating a surface of said first dielectric layer with oxygen plasma;
depositing a second metallic layer above said first dielectric layer;
forming the source and drain electrodes by defining and patterning said second metallic layer; and
forming said sensitive element by filling a channel region of said thin film transistor with an active layer sensitive to said gaseous substance.

12. A method according to claim 11, wherein depositing the first dielectric layer includes depositing a layer of an organic substance or of a metallic-organic compound.

13. A method according to claim 11, wherein said filling includes forming the active layer of at least one among zinc oxide, ternary derivatives of zinc oxide, and quaternary derivatives of zinc oxide.

14. A method
manufacturing a sensor device configured to sense a gaseous substance and including a thin film transistor that includes a source electrode, a drain electrode, a gate electrode, and a sensitive element sensitive to said gaseous substance, said manufacturing including:
forming a first metallic layer on a substrate;
forming said gate electrode by defining and patterning said first metallic layer, wherein defining and patterning said first metallic layer also forms a first plurality of circuit interconnections;
depositing a first dielectric layer above said gate electrode;
depositing a second metallic layer above said first dielectric layer;
forming the source and drain electrodes by defining and patterning said second metallic layer, wherein defining and patterning said second metallic layer also forms a second plurality of circuit interconnections;
forming said sensitive element by filling a channel region of said thin film transistor with an active layer sensitive to said gaseous substance;
forming holes through said first dielectric layer; and
forming conductive paths between said first plurality of circuit interconnections and said second plurality of circuit interconnections.

15. A method according to claim 14, wherein said filling said channel region forms the active layer and includes a layer of zinc oxide or a derivative thereof.

16. A sensor device for sensing a gaseous substance, the sensor device comprising:
a thin film transistor integrated on a substrate and including a source electrode, a drain electrode a gate electrode, a first dielectric layer, and a channel region that includes a sensitive element, the sensitive element including an active layer sensitive to said gaseous substance; and
an encapsulating layer encapsulating said thin film transistor and including a second dielectric layer above said entire thin film transistor, wherein said second dielectric layer is a material that is permeable by said gaseous substance so as to allow said gaseous substance to transport to said sensitive element through said second dielectric layer.

17. A sensor device according to claim 16, wherein said active layer comprises a thin layer of zinc oxide or of a derivative thereof.

18. A sensor device according to claim 16, wherein said active layer comprises zinc oxide nanoparticles and polyaniline nanofibers.

19. A sensor device according to claim 16, wherein said dielectric layer is a layer of an organic substance or of a metallic-organic compound.

20. A sensing system for sensing a gaseous substance, the sensing system comprising:
first and second voltage reference terminals;
a voltage generator configured to generate an input voltage;
an output terminal suitable for supplying an output signal that is varied depending on whether the gaseous substance is detected; and
a sensing transistor and a load transistor coupled to each other between said first and second voltage reference terminal and interconnected in correspondence with said output terminal, said sensing transistor being a thin film transistor that includes a semiconductor channel having an active layer sensitive to said gaseous substance and configured to vary a threshold voltage of said sensing transistor according to an amount of charge entrapped in the active layer as a result of exposure to said gaseous substance.

21. A sensing system according to claim 20, wherein said sensing transistor and said load comprise a CMOS inverter and have respective control terminals coupled to each other and to said voltage generator.

22. A sensing system according to claim 20, wherein said load transistor is a p-type transistor configured to serve as active load.

23. A sensing system according to claim 20, wherein said sensing transistor has a control terminal coupled to said voltage generator and said second load transistor is diode-configured and has a control terminal coupled to said output terminal.

24. A sensing system according to claim 20, wherein said active layer of said sensing transistor comprises a thin layer of zinc oxide or of a derivative thereof.

25. A sensing system according to claim 20, comprising:
an encapsulating layer encapsulating said thin film transistor and including a dielectric layer above said thin film transistor.

26. A sensing system according to claim 25, wherein the encapsulating layer includes an opening through said dielectric layer in correspondence with said active layer of said thin film transistor and configured to directly expose said active layer to said gaseous substance.

27. A sensing system according to claim 25, wherein said dielectric layer is of material permeable to said gaseous substance and is configured to allow said gaseous substance to transport to said active layer through said dielectric layer.

* * * * *